United States Patent [19]

Brown et al.

[11] Patent Number: 5,175,325
[45] Date of Patent: Dec. 29, 1992

[54] PLATINUM COMPLEXES AND USE THEREOF

[75] Inventors: Scott S. D. Brown, Barry, Wales; Peter Y. K. Lo, Midland, Mich.; Richard G. Taylor, Barry, Wales

[73] Assignee: Dow Corning Limited, Barry, Wales

[21] Appl. No.: 810,098

[22] Filed: Dec. 19, 1991

[30] Foreign Application Priority Data

Feb. 14, 1991 [GB] United Kingdom ............... 9103191

[51] Int. Cl.$^5$ ............................................. C07F 15/00
[52] U.S. Cl. ........................................... 556/9; 556/2; 556/136
[58] Field of Search ................ 556/2, 9, 136, 137, 556/431; 514/492

[56] References Cited

U.S. PATENT DOCUMENTS

| | | | |
|---|---|---|---|
| 4,647,679 | 3/1987 | Panster et al. | 556/9 |
| 4,847,228 | 7/1989 | Saruyama | 556/9 X |
| 4,870,062 | 9/1989 | Kurono et al. | 514/492 X |

*Primary Examiner*—Arthur C. Prescott
*Attorney, Agent, or Firm*—William F. Boley

[57] ABSTRACT

Method for preparing a platinum-organosiloxane complex which comprises reacting a platinous halide with an organo-siloxane having from 2 to 4 silicon-bonded organic groups containing terminal olefinic unsaturation, the reaction being carried out in the presence of a polar organic liquid, for example dimethylformamide or butan-2-one, which is at least a partial solvent for the platinous halide.

The acomplexes are useful as catalysts for hydrosilylation reactions.

7 Claims, No Drawings

PLATINUM COMPLEXES AND USE THEREOF

This invention relates to a novel process for the production of complexes of platinum and organosiloxanes and to the use of said complexes.

It is well-known in the art of organosilicon chemistry that organosilicon compounds having silicon-bonded hydrogen atoms can be reacted with organic or organosilicon compounds having ethylenic unsaturation in the presence of a platinum compound as catalyst. The use of chloroplatinic acid as such a catalyst has been described in, for example, G.B.-A-804 097. It is also well-known that the compatibility of chloroplatinic acid in organosilicon reaction mixtures can be improved by reacting the chloroplatinic acid with an organosilicon compound, preferably an organosiloxane, having silicon-bonded unsaturated groups, see for example G.B.-A-1 127 675. A method for preparing platinum complexes of unsaturated siloxanes which are useful as hydrosilylation catalysts is described in U.S. Pat. No. -A-3,775,452. According to said method an unsaturated organosilicon material is mixed with a platinum halide, typically chloroplatinic acid or sodium or potassium chloroplatinate, and the resulting mixture treated with a base to effect the removal of inorganic halogen. Such prior art methods, however, require the presence of water, a very large excess of the vinylsiloxane or long reaction times. The use of a large excess of the vinylsiloxane represents a significant drawback to the method inasmuch as some loss of this relatively expensive reactant occurs as a result of cleavage of the vinyl groups and any remaining excess has to be recovered from the reaction mixture. Further, we have found that the presence of water contributes to the loss of vinyl groups from the siloxane reactant and increases the need for an excess of the vinylsiloxane. It is suggested in U.S. Pat. No. -A-3,775,452 (Col. 7, line 40) that the complex can be recovered in admixture with the excess vinylsiloxane and employed as such. However, the presence of the vinyl-siloxane can reduce the activity of the platinum as a catalyst. Also, such an impure form of the complex may not be satisfactory for certain applications.

We have now found that by employing specific platinum compounds, namely platinous halides, complexes of platinum and organosiloxanes can be obtained by a method which does not require the presence of large excesses of the organo-siloxane or of water. It has been suggested in G.B.-A-1 060 420 that complexes of platinous chloride and unsaturated organosiloxanes can be prepared by direct reaction, as in the case of organic complexes of platinum. However, the yields obtained by such a direct reaction are very low and it is noted that all of the Examples in G.B.-A-1 060 420 illustrate the alternative method described therein which involves the additional step of first forming the organic complex.

According to the present invention there is provided a method for preparing a platinum-organosiloxane complex which comprises reacting a platinous halide with an organo-siloxane in which there are present from 2 to 4 silicon-bonded organic groups having from 2 to 6 carbon atoms and terminal olefinic unsaturation, the remaining silicon-bonded organic substituents being selected from alkyl groups having from 1 to 6 carbon atoms and phenyl groups, said reaction being carried out in the presence of a polar organic liquid which is at least a partial solvent for the platinous halide.

The platinous halide employed in the method of this invention may be $PtCl_2$, $PtBr_2$ or $PtI_2$ but is preferably the more readily available chloride $PtCl_2$.

As the organosiloxane reactant in forming the platinum-organosiloxane complexes there can be employed any cyclic or substantially linear organosiloxanes in which there are from 2 to 4 silicon-bonded organic groups having from 2 to 6 carbon atoms and containing terminal olefinic unsaturation. Such unsaturated groups include hydrocarbon groups for example vinyl, allyl, butenyl and hexenyl but are preferably vinyl. The remaining silicon-bonded organic groups in the organosiloxane reactant are preferably methyl but up to 50% of said remaining groups may be selected from alkyl groups having from 2 to 6 carbon atoms and phenyl groups. Some chain branching may be present in the organo-siloxane reactant. Thus it will have in the molecule from about 1.9 to 3.0 total organic groups per silicon atom. Examples of the operative organosiloxanes are methylvinylcyclotetrasiloxane, copolymers of dimethylsiloxane and methylvinylsiloxane and copolymers of dimethylsiloxane and phenylmethylvinylsiloxane. The preferred organosiloxanes are those in which at least two of the vinyl groups are present on adjacent silicon atoms. Most preferred is 1,3-divinyltetramethyldisiloxane.

The polar organic liquid which must be present in the reaction mixture of the method of this invention should be at least a partial solvent for the platinous halide, that is, it should be capable of solubilising at least some of the platinous halide present in the reaction mixture. It is believed that the reaction proceeds by way of the formation of a weak complex between the polar liquid and the platinous halide. This complex then breaks down and reacts with the organosiloxane via the ligands and olefinic groups to form the desired platinum-organosiloxane complex. Suitable polar organic liquids are therefore those which react with the platinous halide to provide a first complex which is soluble in the polar organic liquid and in which the ligands are displaceable by the olefinic e.g. vinyl groups in the organosiloxane to yield the desired platinum organosiloxane complex. Such polar liquids include amides, for example dimethylformamide, ketones, for example butanone, and acetone and crown ethers, the preferred polar liquids being the amides and ketones. The proportion of polar liquid present is not narrowly critical but preferably falls within the range from 1 to 20 moles of polar liquid per mole of platinous halide.

The organosiloxane is preferably employed in a proportion of at least 3.5 moles per mole of the platinous halide. In order to achieve minimum reaction times the organosiloxane should be present in stoichiometric excess, that is more than 8 vinyl groups per platinum atom. Very large excesses of the organosiloxane are, however, best avoided. We have found that such large excesses can lead to the presence of undesirable amounts of by-product oligomers.

In carrying out the method of this invention the reactants are mixed and reacted at elevated temperatures. Some reaction may occur at temperatures as low as 40° C. but it is preferred to employ temperatures in the range from about 50° C. to 120° C. If desired the reaction may be carried out in the additional presence of a non polar solvent, for example a hydrocarbon solvent such as toluene or xylene. Buffers such as sodium acetate may also be included in the reaction mixture. It is not necessary to dry the reactants beforehand but in order to avoid the formation of undesired oligomeric species the reaction is best carried out in the absence of added water. On completion of the reaction the non polar solvent, if used, may be removed by distillation, if necessary or desired under reduced pressure. The polar organic liquid may be allowed to remain in the platinum siloxane reaction product but can be removed, if desired, under reduced pressure. Where its boiling point permits, any excess of the organo-siloxane reactant may be removed by distillation. However, the platinum-organosiloxane complexes have been found to be unstable during storage in the pure state. If, therefore, the complex is not to be used within a short time after preparation it is preferred to provide it in admixture with a stabilising amount, for example up to 25% by weight, of an organosiloxane having silicon-bonded olefinically-unsaturated groups. Such mixtures may be obtained by allowing some or all of the excess organosiloxane reactant to remain in the product. Alternatively the platinum-organosiloxane may first be isolated and thereafter mixed with the desired olefinically-unsaturated organosiloxane.

The method of this invention has the advantage of providing pure platinum-organosiloxane complexes without the need to use large excesses of the unsaturated organo-siloxane reactant. It can also be carried out in the absence of water, thereby reducing the formation, and presence in the desired product, of oligomeric by-products.

The platinum-organosiloxane complexes prepared by the method of this invention are useful as catalysts. They are particularly useful as catalysts for the well-known hydrosilylation reactions in organosilicon chemistry. In another aspect therefore the invention includes a process comprising reacting (i) a silicon compound having in the molecule at least one silicon-bonded hydrogen atom with (ii) an organic or organosilicon substance containing aliphatic carbon atoms linked by multiple bonds. In such hydrosilylation reactions the organosilicon compounds having $\equiv$SiH groups may be silanes, siloxanes or other silicon containing polymers, for example $HSiCl_3$, $CH_3SiHCl_2$, $HSi(OC_2H_5)_3$, $C_6H_5SiHCl_2$, $C_6H_5SiHCH_3Br$, $(CH_3)_2SiHCl$, $C_2H_5SiH_2Cl$, $CH_3SiH(OCH_3)_2$, methylhydrogen polysiloxanes and copolymers of methylhydrogensiloxane units and, for example, dimethylsiloxane units, trimethylsiloxane units and phenylethylsiloxane units. The nature of the silicon-bonded substituents present in addition to the hydrogen atoms is not critical but normally such substituents will comprise halogen atoms, alkoxy radicals, preferably having less than 6 carbon atoms and monovalent hydrocarbon or halogenated hydrocarbon radicals having from 1 to 18 inclusive carbon atoms.

The compounds containing carbon atoms linked by multiple bonds may be organic, for example pentene-1, hexene-1, heptene-1, acetylene, butadiene, vinylacetylene, cyclohexene, styrene, allyl bromide, vinyl acetate, allyl alcohol or an allyl ether of a poly(alkylene oxide); or they may be organosilicon, for example $(CH_3)_2(CH_2=CH)SiCl$, $(CH_2=CHCH_2)(CH_3)SiBr_2$, $(CH_2=CH)Si(C_2H_5)_2Cl$, $(CH_2=CH)Si(OCH_3)_3$ and organosiloxanes and polysiloxanes containing silicon-bonded vinyl, allyl or hexenyl radicals. Any remaining silicon-bonded substituents in the unsaturated organosilanes and organosiloxanes may be, for example, halogen atoms, alkoxy radicals having less than 6 carbon atoms and monovalent hydrocarbon or halogenated hydrocarbon radicals having from 1 to 18 inclusive carbon atoms.

The reaction of silicon-bonded hydrogen atoms with unsaturated radicals is well-known and may be employed for the preparation of organofunctional and other organosilicon compounds and in the preparation of elastomeric or resinous organosilicon products for coating, encapsulating and other applications. The hydrosilylation reaction may be performed at atmospheric, sub-atmospheric or superatmospheric pressures, in the presence or absence of solvents, and at temperatures ranging from below 20° C. up to and in excess of 150° C.

For certain applications it is desirable to include in compositions comprising (i), (ii) and the platinum catalyst a substance which inhibits and delays the reaction between (i) and (ii). Among known inhibiting substances are the alkyl, alkoxyalkyl and allyl esters of maleic and fumaric acids. According to a further aspect of the invention we have found that, if desired, the platinum-organosiloxane complexes of this invention may be prereacted with such known inhibitor substances to provide a preformed inhibited hydrosilylation catalyst.

The following Examples in which the parts are expressed by weight and viscosities at 25° C. illustrate the invention.

EXAMPLE 1

A mixture of platinum(II)chloride (2.43g, 9.14 mmol), toluene (20cm$^3$), divinyltetramethyldisiloxane (8g, 43 mmol), NaHCO$_3$ (0 3g) and dimethylformamide (0.7g, 9 mmol) was heated to 60–65° C. with stirring for 2 hours. During this time the PtCl$_2$ slowly dissolved to give a yellow solution. The volatiles were then removed under reduced pressure and the residue dissolved in acetone (20cm$^3$). This solution was neutralised with NaHCO$_3$ (2g, excess) followed by removal of the volatiles. The residue was dissolved in toluene (50cm$^3$) and the solution filtered through a column (2 cm$^2 \times$ 10 cm) containing a mixture of diatomaceuous earth and charcoal. The column was washed through with toluene (100 cm$^3$) and the solvent removed from the combined filtrate and washings under reduced pressure (0.1 mmHg) (13.3 Pa) to give a pale yellow oil.

EXAMPLE 2

A mixture of platinum(II)chloride (0.5 g, 1.88 mmol), acetone (5 cm$^3$), divinyltetramethyldisiloxane (1.5 g, 8 mmol), and sodium acetate (0.05 g) was heated to reflux with stirring for 5 hours. During this time the PtCl$_2$ slowly dissolved to give a yellow solution. The residue was neutralised with NaHCO$_3$ (1 g, excess) followed by removal of the volatiles under reduced pressure (0.1 mmHg). The residue was dissolved in hexane (20 cm$^3$) and the solution filtered through a column (2 cm$^2 \times$ 5 cm) containing a mixture of diatomaceuous earth and basic alumina. The column was washed through with hexane (50 cm$^3$) and the solvent removed from the combined filtrate and washings under reduced pressure (0.1 mmHg) (13.3 Pa) to give a pale yellow oil.

EXAMPLE 3

Platinum(II)chloride (10g, 37.6 mmol), divinyltetramethyldisiloxane (68g, 370 mmol) and butan-2-one (50 g) was mixed together in a 250 cm$^3$ flask and placed under an atmosphere of dry nitrogen. The mixture was heated, with stirring, to 75° C. for 5 hours during which time the platinum dichloride dissolved. The reaction mixture was cooled to 25° C. and the volatiles removed under reduced pressure (0.1-0.05 mmHg) (13.3-7 pa) to leave a yellow oil which was then neutralised by adding hexane (25 cm$^3$), sodium bicarbonate and water (1.3 cm$^3$). A further portion of water (1.3 cm$^3$) was added after the initial evolution of $CO_2$ had subsided ca. 20 minutes. After neutralisation was complete (pH 6.5-7.5, universal indicator paper), the mixture was filtered through a pad of diatomaceous filter aid which was then washed with hexane (25 cm$^3$). The volatiles were removed from the filtrate and combined washings under reduced pressure (0.1-0.05mmHg), (13.3-7 Pa) to give the pure platinum complex as a yellow oil (yield 92% based on platinum reactant), containing 24% by weight platinum.

EXAMPLE 4

A mixture consisting of $PtCl_2$ (1.0 g, 3.76 mmoles), tetramethyldivinyldisiloxane (3 g, 16.1 mmoles), butan-2-one (10 g, 0.14 mole) and sodium bicarbonate (0.1 g, 1.19 mmoles) was prepared without taking any precautions to exclude air. The mixture was then heated to 70° C. under an inert atmosphere with stirring. After 4.5 hours the mixture was cooled to ambient temperature and the volatiles removed under reduced pressure (ca. 0.1 mmHg)(13.3 Pa). The residue was then neutralised by adding excess sodium bicarbonate and acetone (10 cm$^3$) and stirring the mixture for 1 hour. Volatiles were again removed under reduced pressure and the residue mixed with hexane (20 cm$^3$) and filtered through a 2 cm × 3 cm pad of Celite ® supported on a medium porosity glass frit. The Celite ® was washed with additional solvent (20 cm$^3$) and the solvent removed from the combined filtrates under reduced pressure to give the pure platinum-organosiloxane complex as a yellow oil (3 g, 85%). This complex (10% by weight) was dissolved in a dimethylvinylsiloxy-terminated polydimethylsiloxane having a viscosity of $45 \times 10^{-5}$ m$^2$/s at 25° C. to provide a storage stable platinum catalyst.

EXAMPLE 5

A composition was prepared by mixing 100 parts of a polydimethylsiloxane having a small proportion of silicon-bonded hexenyl groups and viscosity of $40 \times 10^{-5}$ m$^2$/s, 4 parts of a copolymer of dimethylsiloxane units and methylhydrogensiloxane units and viscosity of $3 \times 10^{-5}$ m$^2$/s, sufficient of the platinum-organosiloxane complex of Example 3 to provide 120 ppm of Pt and a cure inhibitor. The composition was coated on to super calendered Kraft paper which was then placed in an oven at 100° C. The composition cured to form a release coating on the paper after 50 seconds.

EXAMPLE 6

A composition was prepared by mixing 100 parts of a polydimethylsiloxane having terminal silicon-bonded vinyl groups (viscosity $45 \times 10^{-5}$ m$^2$/s), 100 parts of a polydimethylsiloxane (viscosity $2 \times 10^{-5}$ m$^2$/s), 1.2 parts of a low molecular weight copolymer of dimethylsiloxane units, methylhydrogen siloxane units and trimethylsiloxane units and 0.6 part of a catalyst containing 0.5% by weight of Pt which had been prepared by dissolving the product of Example 3 in a liquid polydimethylsiloxane having terminal silicon-bonded vinyl groups.

The composition was allowed to stand at 25° C. and was found to have cured to a gel after 15 minutes.

A similar composition was prepared except that the catalyst component was replaced by 0.175 part of a commercially available platinum-organosiloxane catalyst (PC 072) containing about 3% by weight of Pt. This composition cured to a gel in 18 minutes.

That which is claimed is:

1. A method for preparing a platinum-organosiloxane complex which comprises reacting a platinous halide with an organo-siloxane in which there are present from 2 to 4 silicon-bonded organic groups having from 2 to 6 carbon atoms and terminal olefinic unsaturation, the remaining silicon-bonded organic substituents being selected from alkyl groups having from 1 to 6 carbon atoms and phenyl groups, said reaction being carried out in the presence of a polar organic liquid which is at least a partial solvent for the platinous halide.

2. A method as claimed in claim 1 wherein the polar organic liquid is selected from the group consisting of amides and ketones.

3. A method as claimed in claim 1 wherein the polar organic liquid is present in the reaction mixture in an amount of from 1 to 20 moles per mole of platinous halide.

4. A method as claimed in claim 1 wherein the organosiloxane is employed in an amount of at least 3.5 moles per mole of platinous halide.

5. A method as claimed in claim 1 characterised by the further step of mixing the platinum-organosiloxane complex with a stabilising amount of a liquid organosiloxane having silicon-bonded groups containing terminal olefinic unsaturation.

6. A method as claimed in claim 1 characterised by the further step of reacting the platinum-organosiloxane complex with an ester selected from the group consisting of alkyl, alkoxyalkyl and allyl esters of maleic and fumaric acids.

7. A process which comprises reacting (i) a silicon compound having in the molecule at least one silicon-bonded hydrogen atom with (ii) an organic or organosilicon substance containing aliphatic carbon atoms linked by multiple bonds, said reaction being carried out in the presence of a platinum-organosiloxane complex prepared by the process claimed in claim 1 hereof.

* * * * *